United States Patent
Blenkinsop et al.

(10) Patent No.: US 6,301,979 B1
(45) Date of Patent: Oct. 16, 2001

(54) SAMPLING MEANS

(75) Inventors: Michael Glen Blenkinsop; Roland Arnold Vial, both of Middelburg (ZA)

(73) Assignee: Eskom (ZA)

( * ) Notice: Subject to any disclaimer, the term of this patent is extended or adjusted under 35 U.S.C. 154(b) by 0 days.

(21) Appl. No.: 09/320,976

(22) Filed: May 27, 1999

(30) Foreign Application Priority Data

May 28, 1998 (ZA) ...................................................... 98/4575

(51) Int. Cl.[7] .............................. G01N 1/00; B07B 1/00; G01F 11/00; G01F 13/00
(52) U.S. Cl. ................................. 73/863.51; 73/863.52; 73/863.56; 209/255; 222/226
(58) Field of Search ........................... 73/863.51, 863.52, 73/863.53, 863.54, 863.55, 863.56, 863.57, 863.58, 863.21, 863.71; 222/240, 226; 209/255

(56) References Cited

U.S. PATENT DOCUMENTS

| | | |
|---|---|---|
| 1,860,107 | 5/1932 | Lien . |
| 1,862,250 | 6/1932 | Anderson . |
| 2,044,102 | 6/1936 | Rosewarne . |
| 2,489,592 | 11/1949 | Shaffer . |
| 2,814,204 | 11/1957 | Moyle . |
| 3,060,746 | 10/1962 | Gompper . |
| 3,217,546 | 11/1965 | Cordell . |
| 3,217,547 | 11/1965 | Cordell . |
| 3,383,924 | 5/1968 | Cordell . |
| 4,587,858 | 5/1986 | Bartholomay ..................... 73/863.53 |
| 4,682,507 | * 7/1987 | Terrell .............................. 73/863.57 |
| 4,955,242 | * 9/1990 | Long ................................. 73/863.91 |
| 5,385,058 | * 1/1995 | Krauss .............................. 73/864.32 |

FOREIGN PATENT DOCUMENTS

| | | |
|---|---|---|
| 903119 | 8/1962 | (GB) . |
| 1306077 | 2/1973 | (GB) . |
| 1325864 | 8/1973 | (GB) . |
| 1357600 | 6/1974 | (GB) . |

* cited by examiner

Primary Examiner—Hezron Williams
Assistant Examiner—Dennis S Loo
(74) Attorney, Agent, or Firm—Norris, McLaughlin, Marcus P.A.

(57) ABSTRACT

A sampling means for sampling a falling stream of a particulate material includes a trough-like sampling receptacle for culling a sample of the particulate material, the receptacle having an inlet defined in an operatively top portion thereof and at least one outlet; a shaftless spiral conveyor rotatably received within the receptacle for discharging the sample through the, or each, outlet; drive means operatively connected to the shaftless spiral conveyor for driving the said conveyor; and displacement means for displacing the sampling receptacle between first and second positions on opposed sides of the falling stream of material, to permit the inlet of the sampling receptacle to cut the falling steam of material at pre-determined intervals.

12 Claims, 3 Drawing Sheets

SAMPLING MEANS

FIELD OF THE INVENTION

THIS INVENTION relates to the sampling of particulate materials. More particularly, the invention relates to a sampling means for sampling particulate materials and to a sampling system for sampling particulate materials.

SUMMARY OF THE INVENTION

According to a first aspect of the invention, there is provided a sampling means for sampling a falling stream of a particulate material, the sampling means including a trough-like sampling receptacle for culling a sample of the particulate material, the receptacle having an inlet defined in an operatively top portion thereof and at least one outlet;

a shaftless spiral conveyor rotatably received within the receptacle for discharging the sample through the, or each, outlet;

drive means operatively connected to the shaftless spiral conveyor for driving the said conveyor; and displacement means for displacing the sampling receptacle between first and second positions on opposed sides of the falling stream of material, to permit the inlet of the sampling receptacle to cut the falling stream of material at pre-determined intervals.

A lower portion of the of the sampling receptacle may be semi-circular in cross-section. At least a portion of the top of the sampling receptacle may be open to define the inlet. The inlet may be elongate and rectangular in shape, long sides of the inlet being co-parallel with a receptacle axis. Preferably, the width of the inlet may be between 2.5 and 3 times the top size of the particles of material being sampled. The sampling receptacle may have a single outlet arranged in a bottom of an end region of the trough.

The shaftless spiral conveyor may be rotatably received within the receptacle to fit snugly within the lower semi-circular portion of the receptacle. Preferably, the pitch of the spiral of the shaftless spiral conveyor is at least twice the top size of the particles of the material being sampled.

The drive means may be arranged at an end of the sampling receptacle. The drive means may include an electric motor connected to an end of the shaftless spiral conveyor. The electric motor may be controllable to be actuated at pre-determined intervals to enable the shaftless spiral conveyor to discharge completely each sample culled in a single pass of the sampling receptacle completely before a further pass of the receptacle. Instead, the speed of the electric motor may be controlled so that the shaftless spiral conveyor operates continuously, discharging samples as they are culled.

The displacement means may displace the sampling receptacle reciprocally between its first and second positions. The displacement means may include a linear conveyor for displacing the sampling receptacle laterally and reciprocally through the falling stream between the first position on a first side of the falling stream to the second position on an opposed second side of the falling stream. Preferably, the inlet of the trough shall be clear of the falling stream when the trough is in the first and second positions. Further, preferably, the inlet of the trough is dimensioned so that the length of the inlet is at least as great as the width of the falling stream, so that the entire falling stream is cut with each pass of the sampling receptacle.

In a further embodiment of the invention, the sampling receptacle may have a pair of outlets, each outlet arranged in a respective end portion of the receptacle and the shaftless spiral conveyor may comprises two spiral portions of opposite pitch direction. The shaftless spiral conveyor may be driven by a single drive means, which may comprise an electric motor.

The sampling means may include a crusher for reducing mean particle size of the particulate material to be sampled and to reduce a variation of particle sizes within the material to be sampled.

According to a second embodiment of the invention, there is provided a sampling system for sampling a falling stream of a particulate material, the sampling system including a first sampling means including a trough-like sampling receptacle for culling a sample of the falling stream of particulate material, the receptacle having an inlet defined in an operatively top portion thereof and at least one outlet; a shaftless spiral conveyor rotatably received within the receptacle for discharging the sample through the, or each, outlet; a drive means operatively connected to the shaftless spiral conveyor for driving the said conveyor; and displacement means for displacing the sampling receptacle between first and second positions on opposed sides of the falling stream of material, to permit the inlet of the sampling receptacle to cut the falling stream of material of pre-determined intervals; and at least one further sampling means arranged in series with the first sampling means, the, or each, further sampling means including a trough-like sampling receptacle for culling a further sample of particulate material from a subsidiary falling stream of particulate material comprising sample material discharged through the, or one of the, outlets an adjacent upstream sampling means, the receptacle having an inlet defined in an operatively top portion thereof and at least one outlet; a shaftless spiral conveyor rotatably received within the receptacle for discharging the further sample through the, or each, outlet; a drive means operatively connected to the shaftless spiral conveyor for driving the said conveyor; and displacement means for displacing the sampling receptacle between first and second positions on opposed sides of the subsidiary falling stream of material, to permit the inlet of the sampling receptacle to cut the subsidiary falling stream of material at pre-determined intervals.

The invention is now described, by way of example, with reference to the accompanying diagrammatic drawings.

DETAILED DESCRIPTION OF THE DRAWINGS

Figure 1:
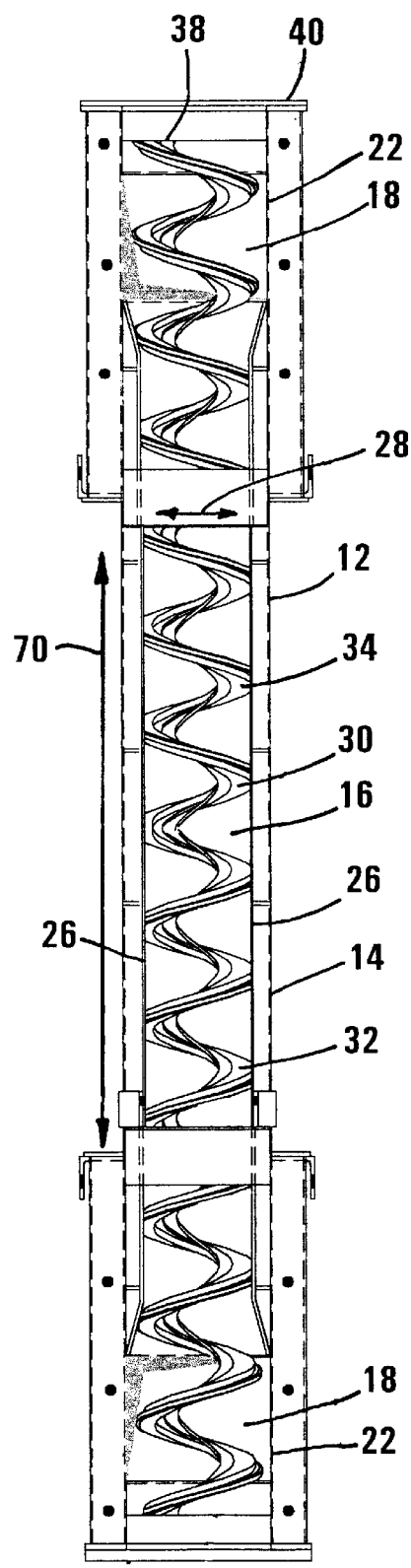
FIG. 1 shows a trough-like sampling receptacle of a sampling means, in accordance with the invention, for sampling particulate materials.

In the drawings, reference numeral 10 generally indicates a sampling means, in accordance with the invention, for sampling particulate materials.

The sampling means 10 includes a trough-like sampling receptacle 12 for receiving a sample. As shown in FIG. 1, an open top portion 14 of the trough 12 defines an inlet 16. A pair of outlets 18 are defined in a bottom 20 of the trough and in end regions 22 thereof. An operatively lower portion 24 of the trough 12 is semi circular in cross-section. The inlet 16 is elongate rectangular in shape, long sides 26 of the inlet 16 being co-parallel with a trough axis. The width 28 of the inlet 16 is 2.5 times the top size of the material being sampled.

The sampling means 10 includes a shaftless spiral conveyor 30. The shaftless spiral conveyor 30 is rotatably received within the trough 12 to fit snugly within this lower semi-circular portion 24 of the trough 12. As shown in FIG. 1, the shaftless spiral conveyor 30 comprises first and second portions 32 and 34, each of which is half the length of the shaftless spiral conveyor 30. The first and second portions 32 and 34 have opposed pitch directions. The pitch of each portion 32 and 34 of the spiral conveyor 30 is at least twice the top size of the particles of material being sampled. An electric motor 36 (shown in FIG. 2) is connected to an end 38 of the shaftless spiral conveyor 30. The electric motor 36 is mounted on an end wall 40 of the trough 12. The speed of the electric motor 36 is controllable and may be connected so that the spiral conveyor 30 operates continuously to discharge a continuous falling stream of sampled material through the outlets 18.

Figure 2:
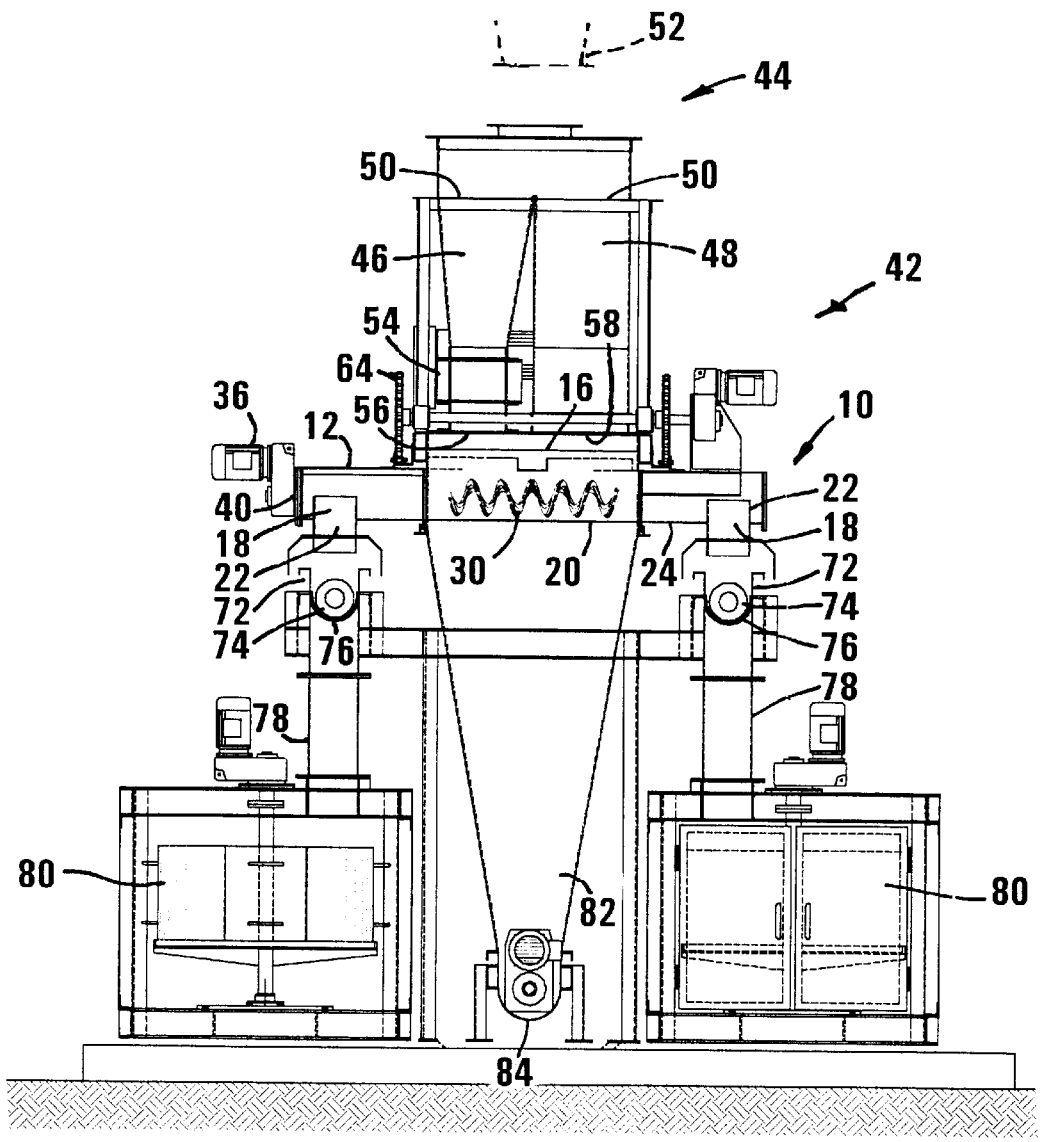
FIG. 2 shows a partly cut away sectional front view of a sampling means, in accordance with the invention, for sampling particulate materials.
Figure 3:
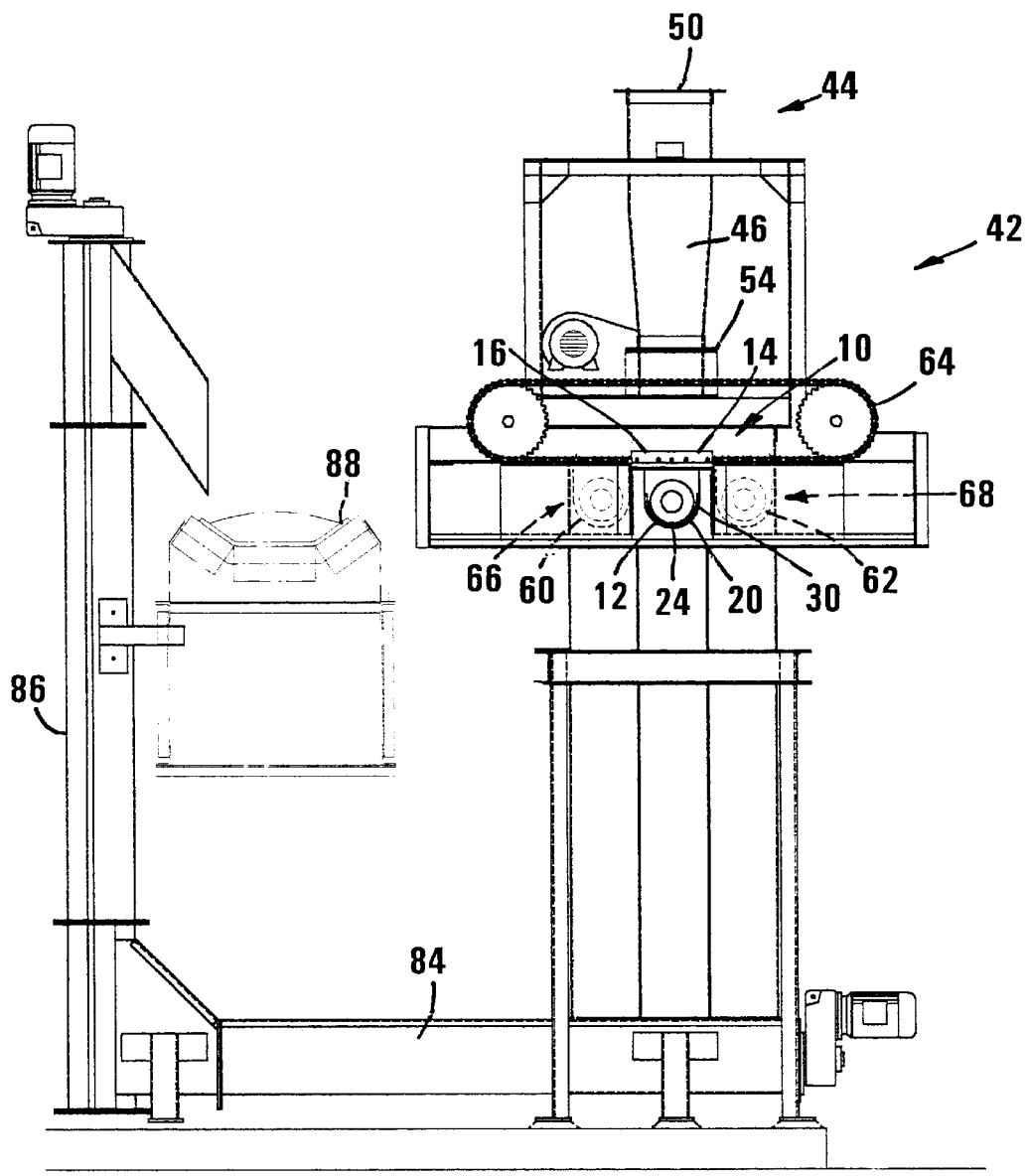
FIG. 3 shows a sectional side view of the sampling means.

We now turn to FIGS. 2 and 3 which show a sampling means 10 in use in a system 42 for sampling coal for burners of a coal-fired power station. In FIGS. 2 and 3, with reference to FIG. 1, like numerals refer to like components unless otherwise indicated.

The system 42 has a supply means 44 for supplying a falling stream of particulate material to be sampled. The supply means 44 includes a pair of inlet chutes 46 and 48 which are arranged side-by-side. Each inlet chute 46 and 48 has an inlet 50 for receiving the particulate material to be sampled. The particulate material is provided via a feed chute 52, fed by a materials conveyor (not shown). The inlet chute 46 feeds material to a crusher 54 and particulate material, having passed through the crusher 54, is supplied in a falling stream via an outlet 56. In the case of inlet chute 48, an uninterrupted falling stream of particulate material is supplied via an outlet 58. The two outlets 56 and 58 of the inlet chutes 46 and 48, respectively, are arranged side-by-side to provide two parallel primary falling streams of particulate material.

A sampling means 10 is arranged below the outlets 56 and 58 and is displaceable between first and second positions 60 and 62, as shown in FIG. 3, on opposed sides of the primary falling streams. The sampling means 10 is arranged on a chain drive 64 to be displaced in a direction perpendicular to the longitudinal axis of the trough 12, laterally through the primary falling streams from the first position 60 on a first side 66 of the falling streams to the second position 62 on an opposed second side 68 of the falling streams. The inlet 16 of the trough 12 is clear of the falling streams when the trough 12 is in the first and second positions 60 and 62. Further, the inlet 16 of the trough 12 is dimensioned so that the length 70 of the inlet 16 is at least as great as the combined width of the falling streams, so that the entire falling streams are cut with each pass of the sampling means 10. The sample of particulate material sampled by the sampling means 10 is discharged via the outlets 18 into a pair of stationary troughs 72, each of which has a shaftless screw conveyor 74. The longitudinal axes of the troughs 72 are perpendicular to the longitudinal axis of the trough 12. The screw conveyors 74 convey the samples via outlets 76 and conduits 78 to feed a pair of rotary samplers 80. Those familiar with the art will appreciate that the rotary samplers 80 further divide the sample provided, by displacing a series of buckets (not shown) of the samplers 80 in rotation to cut a respective sample stream.

That part of the falling streams which is not sampled by the sampling means 10 falls via a third chute 82 onto a further shaftless spiral conveyor 84 from which it is conveyed via a still further shaftless spiral conveyor 86 onto a belt conveyor 88 for processing in the burners.

It will be appreciated that further sets of sampling means 10 and stationary troughs having shaftless spiral conveyors, such as 72 and 74, may be stacked in series to further split the sample, if required.

By means of the invention there is provided a sampling means 10 for sampling particulate material, which is simple to operate and manufacture and which has the advantage that the particulate material is inhibited from building up and adhering to the sampling receptacle 12. The shaftless spiral conveyor 30 inhibits such particulate build-up which, it will be appreciated, impacts negatively on sampling accuracy and necessitates continuous cleaning of the sampling receptacle 12. The displacement speed and interval between passes of the sampling receptacle 12 in cutting the sample stream may be controlled to meet pre-determined sampling criteria, and may be adjusted to suit particular circumstances. Further, the rotational speed of the shaftless spiral conveyor 30 may be controlled to provide a continuous output stream of material sampled, rather than a series of sample batches. This permits efficient and smooth continuous sampling of the particulate materials. Moreover, it will be appreciated that shaft-mounted spiral conveyors have certain limitations which are not present with shaftless spiral conveyors 30. Importantly, shaftless spiral conveyors 30 need not be journalled onto bearings, thereby reducing costs of manufacture and maintenance costs related to such bearings. Further, shaft-mounted spiral conveyors are generally limited to handling material in a trough 12 up to a maximum level below the level of the shaft of the conveyor. Since this is not a limitation in the case of shaftless conveyors, the overall dimensions of both the trough 12 and shaftless spiral conveyor 30 may be smaller than would be required for sampling the same quantity of material using a shaft-mounted spiral conveyor and sampling trough. For this reason, sampling systems 42 may be reduced in size where sampling means 10 as provided in this invention are used. Still further, shaft-mounted spiral conveyors in sampling troughs tend to damage particulate materials, thereby altering the particle size of the particulate material, as sampled. The resulting sample is then not be representative of the material being sampled. Further, a plurality of such sampling means 10 may be stacked in series, thereby enabling samples of manageable size to be taken and enabling a reduction in the physical space occupied a sampling system 42.

What is claimed is:

1. In a sampling means for sampling a falling stream of a particulate material, the sampling means including
   a trough-like sampling receptacle for culling a sample of the particulate material, the receptacle having an inlet defined in an operatively top portion thereof and at least one outlet;
   a spiral conveyor rotatably received within the receptacle for discharging the sample through the at least one outlet;
   drive means operatively connected to the shaftless spiral conveyor for driving the said conveyor; and
   displacement means for displacing the sampling receptacle between first and second positions on opposed sides of the falling stream of material, wherein the spiral conveyor is a shaftless spiral conveyor, and the displacement means permits the inlet of the sampling receptacle to cut the falling stream of material at pre-determined intervals.

2. The sampling means as claimed in claim 1, in which the a lower portion of the of the sampling receptacle is semi-circular in cross-section.

3. The sampling means as claimed in claim 2, in which at least a portion of the top of the sampling receptacle is open to define the inlet.

4. The sampling means as claimed in claim 3, in which the sampling receptacle has a single outlet arranged in a bottom of an end region of the trough.

5. The sampling means as claimed in claim 4, in which the drive means is arranged at an end of the sampling receptacle.

6. The sampling means as claimed in claim 5, in which the drive means includes an electric motor connected to an end of the shaftless spiral conveyor.

7. The sampling means as claimed in claim 6, in which the electric motor is controllable to be actuated at pre-determined intervals.

8. The sampling means as claimed in claim 1, in which the sampling receptacle has a pair of outlets, each outlet arranged in a respective end portion of the receptacle and the shaftless spiral conveyor comprises two spiral portions of opposite pitch direction.

9. The sampling means as claimed in claim 1, in which the displacement means displaces the sampling receptacle reciprocally between its first and second positions.

10. The sampling means as claimed in claim 9, in which the displacement means includes a linear conveyor for displacing the sampling receptacle laterally and reciprocally through the falling stream between its first and second positions.

11. The sampling means as claimed in claim 1, which includes a crusher for reducing mean particle size of the particulate material to be sampled and to reduce a variation of particle sizes within the material to be sampled.

12. In a sampling system for sampling a falling stream of a particulate material, the sampling system including a first sampling means including a trough-like sampling receptacle for culling a sample of the falling stream of particulate material, the receptacle having an inlet defined in an operatively top portion thereof and at least one outlet; a spiral conveyor rotatable received within the receptacle for discharging the sample through the at least one outlet; a drive means operatively connected to the spiral conveyor for driving the said conveyor; and displacement means for displacing reciprocally the sampling receptacle between first and second positions on opposed sides of the falling stream of material; and at least one further sampling means arranged in series with the first sampling means, the, or each, further sampling means including a trough-like sampling receptacle for culling a further sample of particulate material from a subsidiary falling stream of particulate material comprising sample material discharged through the, or one of the, outlets an adjacent upstream sampling means, the receptacle having an inlet defined in an operatively top portion thereof and at least one outlet; a spiral conveyor rotatably received within the receptacle for discharging the further sample through the, or each, outlet; a drive means operatively connected to the spiral conveyor for driving the said conveyor; and displacement means for displacing reciprocally the sampling receptacle between first and second positions on opposed sides of the subsidiary falling stream of material, wherein each spiral conveyor is a shaftless spiral conveyor, and each displacement means permits the inlet of the sampling receptacle to cut the falling streams of material at pre-determined intervals.

\* \* \* \* \*